US00PP08297P

United States Patent [19]

Olmo

[11] Patent Number: Plant 8,297

[45] Date of Patent: Jul. 13, 1993

[54] "3-14-71" GRAPEVINE

[75] Inventor: Harold P. Olmo, Davis, Calif.

[73] Assignee: Marko Zaninovich, Inc., Delano, Calif.

[21] Appl. No.: 709,240

[22] Filed: Jun. 3, 1991

[51] Int. Cl.[5] ..... A01H 5/00

[52] U.S. Cl. ..... Plt./47.1

[58] Field of Search ..... Plt. 47, 47.1

*Primary Examiner*—James R. Feyrer

*Attorney, Agent, or Firm*—Worrel & Worrel

[57] ABSTRACT

A new and distinct variety of grapevine producing fruit of dark red to black coloration which is mature for harvesting and shipment approximately two weeks after the "Thompson Seedless" grapevine and is of large size and possessing an exceptional ability to retain its freshness and flavor long after harvest and in cold storage.

1 Drawing Sheet

BACKGROUND OF THE NEW VARIETY

The present invention relates to a new and distinct variety of grapevine, which will hereinafter be denominated varietally as "3-14-71", and more particularly to a grapevine of the vinifera species characterized by large seedless berries of dark red to black color; which is mature for commercial harvesting approximately September 28th in McFarland, Calif.; and which has an exceptional ability to retain its freshness and palatability long after harvest during shipping, handling and in cold storage.

The "Thompson Seedless" grapevine is a variety which has been one of the most commercially successful producing large, green seedless berries of good flavor, ripening for harvest beginning in August and extending to mid September in the San Joaquin Valley of central California. Because of these attributes and because of the exceptional shipping and handling characteristics of the fruit as well as other factors, the "Thompson Seedless" grapevine has been one of the most extensively planted grapevine varieties in the San Joaquin Valley over many decades to whose climate it is uniquely well suited. Furthermore, the fruit of the "Thompson Seedless" grapevine has been well received in the marketplace.

In the marketing of grapes, which may generally be classified as to coloration as being either "green" or "colored", it is known that for any given segment of the season it is desirable to have fruit of both color types available for sale. The green class of grape varieties may vary in color form yellow-white to relatively deep green. The colored class of grape varieties may vary in color from red to black. During some portions of the season for grapes, there are varieties of both general color types available which have more or less compatible characteristics, in that they are seedless, flavorful and durable through harvesting, shipping and in cold storage. It has been found that during any such segment of the season, purchasers may exhibit a predilection for either color or both color types.

During the segment of the season occupied by the "Thompson Seedless" grapevine, there has not heretofore been a colored grape variety available having truly comparable attributes to those of the grapes of the "Thompson Seedless" grapevine. As a consequence, the development of a new colored grape variety having characteristics much more closely approaching those of the "Thompson Seedless" grapevine has been an objective long sought, but not heretofore achieved.

The "3-14-71" grapevine of the present invention is the result of an extensive breeding project directed toward the development of just such a new grapevine variety and which has been found substantially to achieve the objectives of that project in providing a grapevine producing a colored seedless grape ripening for harvest substantially later than the fruit of the "Thompson Seedless" grapevine and otherwise having attributes compatible therewith. The new variety is distinctly different from the "Thompson Seedless" grapevine. It fills a niche in the marketing season by offering a large seedless berry that is colored, maturing after the main harvest of "Thompson Seedless" grapevine.

ORIGIN AND ASEXUAL REPRODUCTION OF THE NEW VARIETY

The present variety of grapevine hereof resulted from a breeding project in which the selections were of complicated parentage, involving a number of progenitors. The parentage of the new variety is Hunisa, O.P. by Q25-6. A large berried selection of Hunisa grown for open-pollinated (O.P.) seed was used as a female parent. The pollen parent, the seedless variety Q25-6, was developed after several generations of crossing "Emperor" grapevines with a series of unnamed seedless selections. The cross which produced the parent grapevine of the new variety was made by the inventor in 1982 at Davis, Calif. The seedling of the new variety was planted near Richgrove, Calif. and bore its first fruit in 1985. The new variety was selected for asexual reproduction for all of the attributes hereinafter set forth. Cuttings were taken from the parent grapevine of the new variety in January 1986 and used asexually to reproduce the new variety in a planting at McFarland, Calif. The clonal progeny of the new variety were observed through several growing seasons and bore their first fruit in 1988. The inventor has confirmed through such observation that the clonal progeny of the new variety precisely retained those distinctive attributes which caused the parent of the new variety to be selected for asexual reproduction as hereinafter set forth.

SUMMARY OF THE NEW VARIETY

The grapevine is characterized as to novelty by producing large seedless grapes of a dark red to black coloration, having excellent durability during harvesting, handling and while in cold storage retaining its original fresh and flavorable character long after harvest. The grapevine of the subject invention has a high and uniform fruitfulness of basal buds, permitting short pruning and more economic production. The fruit produced by the "3-14-71" grapevine is ripe for commercial harvesting and shipment about two weeks later than the "Thompson Seedless" grapevine.

BRIEF DESCRIPTION OF THE DRAWING

The accompanying drawing is a color photograph of representative portions of the new grapevine of the present invention including bunches of grapes and sectioned portions of individual berries thereof, those on the left of center being in their natural form as described herein and those on the right of center being in the form resulting from treatments with gibberellic acid; and typical foliage and canes of the new variety.

DETAILED DESCRIPTION

Referring more specifically to the viticultural details of this new and distinct variety of grapevine, the following has been observed under the ecological conditions prevailing at a vineyard located in McFarland, Calif. All major color code designations are by reference to the *Nickerson Color Fan* published by Munsell Color Co. Incorporated. Common color names are also occasionally employed.

VINE

Generally:

*Size.*—Large.

*Form.*—Upright in growth habit, shoots slender and straight with long internodes. Bud burst in mid season.

*Vigor.*—Vigorous.

*Shoot tip.*—Open vinifera type. Internodes striped red on dorsal side with very sparse hairiness. No or feeble hairiness on nodes. Shoot tip reddish overall. Tendrils — thin, trifid and very long and coiling readily on support.

Productivity: This new variety is highly fruitful, even the basal buds produce fruit clusters of commercial value. Thus, short spur pruning can be utilized, providing a more economic system that the long canes necessary for most seedless varieties.

Canes: Erect, ellipsoidal in cross section.

*Surface.*—Very smooth and glabrous.

*Color.*—Dark orange yellow (10 Y 6/8).

*Color — nodes and faint striations.*—Moderate yellowish-brown (10 YR 4/4).

*Nodes.*—Generally — Not prominent.

*Internode length.*—Long straight.

*Dormant buds.*—Conical, pointed and well-sealed.

*Flowers.*—Generally — Hermaphrodite, stamens with erect and long filaments. Uniform in opening and shedding of pollen and calyptra.

*Date of Bloom.*—In McFarland, Calif. — May 5th. In Richgrove, Calif. — May 6th.

*Berries.*—Seedless, although there are often two collapsed and soft rudiments 3 mm (0.118 inches) to 5 mm (0.196 inches) in length that do not become gritty.

LEAVES

Size:

*Generally.*—Large. Three lobed, central lobe of blade cupped inward, often resulting in the superior sinuses, which are narrow and deep, being closed by the overlapping lobes.

*Average length.*—22.8 cm (8.976 inches).

*Average width.*—21.8 cm (8.582 inches).

Form: Outline — wedge-shaped.

Color — leaf blade: Dark green, dull aspect when fully expanded, glabrous except for few sparse arachnoid tufts between larger lateral veins.

Teeth: Very large, acute, rectilinear. Apical teeth on lateral lobes are often more prominent than the terminal one of the central lobe. This is a good mark of identification.

Teeth — Number: Few.

Color — Leaf: Veins on underside whitish in contrast.

Petiolar sinus: Narrow, V-shaped to lyre, closed.

Petiole:

*Length.*—Equal to that of the midrib.

*Thickness.*—Medium.

*Color.*—Pink at juncture with leaf blade.

Stipules: Not distinctive.

FRUIT

Maturity when described: Ripe for commercial harvesting and shipment in McFarland in the San Joaquin Valley of central California, on September 28th and in Richgrove, Calif., on October 1st. The fruit description refers to natural clusters arising from the first basal buds of medium canes borne on mature vines trained as bilateral cordons. The very high fruitfulness of basal buds permits very short spur pruning in the dormant period and later regulation and selection of the best clusters by deshooting.

Cluster:

*Generally.*—Conical and borne on nodes two and three, well filled, with peduncle offset from the cane.

*Measuring from point of attachment.*—Approximately 2.1 cm (0.826 inches) to first tendril branch, thence 3.7 cm (1.456 inches) to first fruiting branch, plus 24.8 cm (9.763 inches) of fruiting area to tip of the cluster.

*Width.*—12.7 cm (5 inches). Overall weight of the cluster is 446 g, (15.928 ounces) of which the stem structure (rachis) accounts for about 1.8 percent of the fresh weight. The mean number of berries per cluster is about 175, with less than one percent small (shot) berries. If longer spurs or canes are left at pruning time, the clusters are much larger in size, in which case, a winged or double cluster can arise.

*Peduncle.*—Medium width, woody only at point of attachment, rachis retains a bright green color for a very long time post-harvest. The berries retain their freshness and flavor after long periods of cold storage.

Berry: Ellipsoidal, flattened at point of attachment, 19 mm (0.748 inches)×22 mm (0.866 inches); mean weight of 10 largest berries per cluster 35.5 g (1.267 ounces); berry size increased substantially by girdling.

*Berry color.*—Varies from dark red to black depending on relative maturity.

Flesh:

*Generally.*—Meaty and firm.

*Texture.*—Skin is thin.

*Juice.*—Uncolored.

*Flavor.*—Neutral.

*Aroma.*—Not distinctive.

*Ripening.*—Late September to mid October at McFarland, Calif.

*Eating quality.*—Very good.

Seeds: Seedless, occasionally small rudiments that remain soft and unobjectionable.

use: Table grapes.

Shipping, handling and storage qualities: Excellent.

Although the new variety of grapevine possesses the described characteristics noted above as a result of the growing conditions prevailing in McFarland in the San Joaquin Valley of central California, it is to be understood that variations of the usual magnitude and characteristics incident to changes in growing conditions, fertilization, pruning, chemical treatment, irrigation and pest control are to be expected.

Have thus described and illustrated my new variety of grapevine, what I claim as new and desire to be secured by Plant Letters Patent is:

1. A new and distinct variety of grapevine substantially as illustrated and described having buds which are highly fruitful, permitting short pruning and selective use of best fruit clusters and which produces seedless fruit of dark red to black coloration which are mature for commercial harvesting and shipment approximately September 28th in McFarland in the San Joaquin Valley of central California and which further has excellent shipping, handling and cold storage quality retaining its freshness and flavor long after harvest.

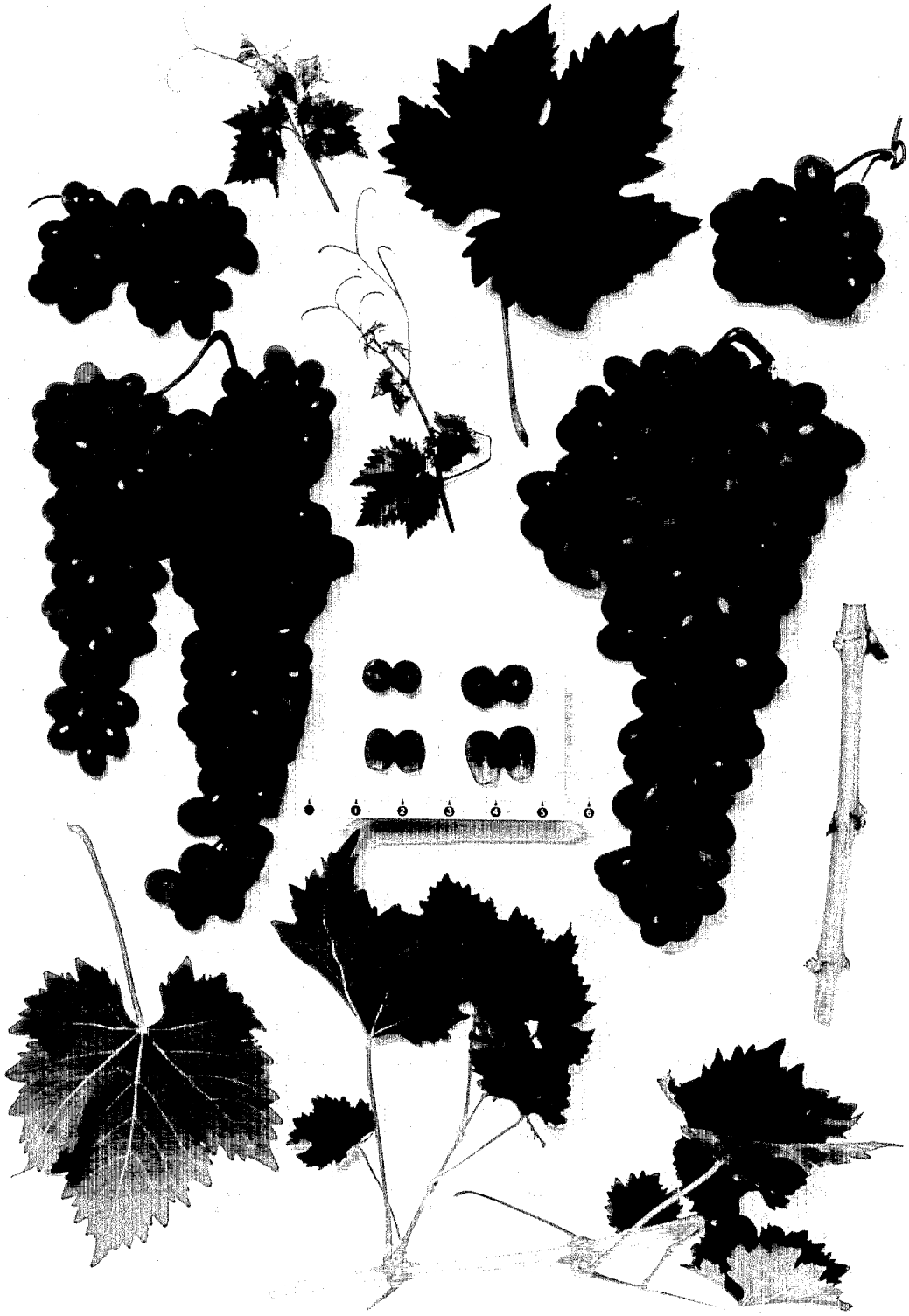

* * * * *